(12) United States Patent
Dalton

(10) Patent No.: US 8,048,131 B2
(45) Date of Patent: Nov. 1, 2011

(54) POLYAXIAL LOCKING SCREW PLATE ASSEMBLY

(75) Inventor: Brian E. Dalton, Erie, PA (US)

(73) Assignee: Aesculap Implant Systems, LLC, Center Valley, PA (US)

( * ) Notice: Subject to any disclaimer, the term of this patent is extended or adjusted under 35 U.S.C. 154(b) by 950 days.

(21) Appl. No.: 11/899,702

(22) Filed: Sep. 7, 2007

(65) Prior Publication Data

US 2008/0004627 A1 Jan. 3, 2008

Related U.S. Application Data

(62) Division of application No. 10/788,098, filed on Feb. 26, 2004, now Pat. No. 7,311,712.

(51) Int. Cl.
*A61B 17/86* (2006.01)
*A61F 2/08* (2006.01)
(52) U.S. Cl. ....................................................... 606/305
(58) Field of Classification Search .................. 606/300, 606/301, 304, 305, 313; 411/271, 325, 354, 411/355
See application file for complete search history.

(56) References Cited

U.S. PATENT DOCUMENTS

| | | | |
|---|---|---|---|
| 4,463,753 A | 8/1984 | Gustilo | |
| 4,484,570 A | 11/1984 | Sutter et al. | |
| 5,129,899 A | 7/1992 | Small et al. | |
| 5,147,363 A | 9/1992 | Härle | |
| 5,211,647 A | 5/1993 | Schmieding | |
| 5,269,784 A | 12/1993 | Mast | |
| 5,486,176 A | 1/1996 | Hildebrand et al. | |
| 5,520,690 A | 5/1996 | Errico et al. | |
| 5,531,746 A | 7/1996 | Errico et al. | |
| 5,540,690 A | 7/1996 | Miller et al. | |
| 5,607,426 A | 3/1997 | Ralph et al. | |
| 5,620,443 A | 4/1997 | Gertzbein et al. | |
| 5,643,265 A | 7/1997 | Errico et al. | |
| 5,669,911 A | 9/1997 | Errico et al. | |
| 5,735,853 A | 4/1998 | Olerud | |
| 5,749,916 A | 5/1998 | Richelsoph | |
| 5,797,911 A | 8/1998 | Sherman et al. | |
| 5,800,433 A | 9/1998 | Benzel et al. | |
| 5,863,293 A | 1/1999 | Richelsoph | |

(Continued)

FOREIGN PATENT DOCUMENTS

DE 200 01 879 3/2000

(Continued)

OTHER PUBLICATIONS

English Translation of Office Action in Chinese Patent Application 2005800005840.6, mailed Feb. 15, 2008.

(Continued)

*Primary Examiner* — Anu Ramana
(74) *Attorney, Agent, or Firm* — RatnerPrestia

(57) ABSTRACT

A bone fixation screw includes a threaded screw shank and a screw head having upper and lower ends. The screw head lower end is secured to a proximal end of said screw shank. The screw head has substantially frustospherical shaped side surfaces and is split into segments at one of the ends. The head is radially expandable at the one end. An expansion screw is centrally received in the screw head. An interface between the expansion screw and the screw head forms a cam mechanism for expanding the screw head upon axial rotation of the expansion screw.

16 Claims, 4 Drawing Sheets

U.S. PATENT DOCUMENTS

| | | | |
|---|---|---|---|
| 5,876,402 A | 3/1999 | Errico et al. | |
| 5,879,350 A | 3/1999 | Sherman et al. | |
| 5,885,286 A | 3/1999 | Sherman et al. | |
| 5,910,142 A * | 6/1999 | Tatar | 606/272 |
| 5,954,635 A | 9/1999 | Foley et al. | |
| 5,954,722 A | 9/1999 | Bono | |
| 5,964,760 A | 10/1999 | Richelsoph | |
| 5,976,141 A | 11/1999 | Haag et al. | |
| 5,976,187 A | 11/1999 | Richelsoph | |
| 6,022,350 A | 2/2000 | Ganem | |
| 6,030,389 A | 2/2000 | Wagner et al. | |
| 6,033,406 A | 3/2000 | Mathews | |
| 6,053,917 A | 4/2000 | Sherman et al. | |
| 6,074,391 A | 6/2000 | Metz-Stavenhagen et al. | |
| 6,083,225 A | 7/2000 | Winslow et al. | |
| 6,096,038 A | 8/2000 | Michelson | |
| 6,132,432 A | 10/2000 | Richelsoph | |
| 6,146,386 A | 11/2000 | Blackman et al. | |
| 6,152,871 A | 11/2000 | Foley et al. | |
| 6,159,179 A | 12/2000 | Simonson | |
| 6,162,170 A | 12/2000 | Foley et al. | |
| 6,171,311 B1 | 1/2001 | Richelsoph | |
| 6,197,033 B1 | 3/2001 | Haid, Jr. et al. | |
| 6,200,322 B1 | 3/2001 | Branch et al. | |
| 6,206,822 B1 | 3/2001 | Foley et al. | |
| 6,217,509 B1 | 4/2001 | Foley et al. | |
| 6,235,033 B1 | 5/2001 | Brace et al. | |
| 6,248,105 B1 | 6/2001 | Schlapfer et al. | |
| 6,261,291 B1 | 7/2001 | Talaber et al. | |
| 6,280,442 B1 | 8/2001 | Barker et al. | |
| 6,280,445 B1 | 8/2001 | Morrison et al. | |
| 6,287,311 B1 | 9/2001 | Sherman et al. | |
| 6,290,703 B1 | 9/2001 | Ganem | |
| 6,299,616 B1 | 10/2001 | Beger | |
| 6,328,738 B1 | 12/2001 | Suddaby | |
| 6,328,740 B1 | 12/2001 | Richelsoph | |
| 6,328,741 B1 | 12/2001 | Richelsoph | |
| 6,331,179 B1 | 12/2001 | Freid et al. | |
| RE37,665 E | 4/2002 | Ralph et al. | |
| 6,402,752 B2 | 6/2002 | Schäffler-Wachter et al. | |
| 6,402,756 B1 | 6/2002 | Ralph et al. | |
| 6,402,757 B1 * | 6/2002 | Moore et al. | 606/80 |
| 6,428,542 B1 | 8/2002 | Michelson | |
| 6,451,021 B1 | 9/2002 | Ralph et al. | |
| 6,488,459 B2 * | 12/2002 | Carpenter | 411/325 |
| 6,514,260 B1 | 2/2003 | Zdeblick et al. | |
| 6,520,907 B1 | 2/2003 | Foley et al. | |
| 6,527,776 B1 | 3/2003 | Michelson | |
| 6,530,929 B1 | 3/2003 | Justis et al. | |
| 6,533,786 B1 | 3/2003 | Needham et al. | |
| 6,562,046 B2 | 5/2003 | Sasso | |
| 6,565,565 B1 | 5/2003 | Yuan et al. | |
| 6,575,899 B1 | 6/2003 | Foley et al. | |
| 6,575,975 B2 | 6/2003 | Brace et al. | |
| 6,599,290 B2 | 7/2003 | Bailey et al. | |
| 6,602,255 B1 | 8/2003 | Campbell et al. | |
| 6,623,485 B2 | 9/2003 | Doubler et al. | |
| 6,645,207 B2 | 11/2003 | Dixon et al. | |
| 6,663,616 B1 | 12/2003 | Roth et al. | |
| 6,682,534 B2 | 1/2004 | Patel et al. | |
| 6,695,772 B1 | 2/2004 | Bon et al. | |
| 6,695,846 B2 | 2/2004 | Richelsoph et al. | |
| 6,712,818 B1 | 3/2004 | Michelson | |
| 6,712,819 B2 | 3/2004 | Zucherman et al. | |
| 6,780,185 B2 | 8/2004 | Frei et al. | |
| 6,780,186 B2 | 8/2004 | Errico et al. | |
| 7,118,303 B2 * | 10/2006 | Doubler et al. | 403/362 |
| 2001/0014807 A1 | 8/2001 | Wagner et al. | |
| 2001/0034521 A1 | 10/2001 | Bailey et al. | |
| 2001/0037111 A1 | 11/2001 | Dixon et al. | |
| 2002/0016595 A1 * | 2/2002 | Michelson | 606/73 |
| 2002/0161368 A1 | 10/2002 | Foley et al. | |
| 2002/0183754 A1 | 12/2002 | Michelson | |
| 2003/0045875 A1 | 3/2003 | Bertranou | |
| 2003/0060826 A1 | 3/2003 | Foley et al. | |
| 2003/0073996 A1 | 4/2003 | Doubler et al. | |
| 2003/0078583 A1 | 4/2003 | Biedermann et al. | |
| 2003/0149431 A1 | 8/2003 | Varieur | |
| 2003/0208203 A1 | 11/2003 | Lim et al. | |
| 2003/0216735 A1 | 11/2003 | Altarac et al. | |
| 2004/0039384 A1 | 2/2004 | Boehm, Jr. et al. | |
| 2004/0127897 A1 | 7/2004 | Freid et al. | |
| 2004/0133207 A1 | 7/2004 | Abdou | |

FOREIGN PATENT DOCUMENTS

| | | |
|---|---|---|
| EP | 1 364 623 | 11/2003 |
| WO | WO 88/03781 | 6/1988 |
| WO | WO 96/08206 | 3/1996 |
| WO | WO 96/25892 | 8/1996 |
| WO | WO 96/32071 | 10/1996 |
| WO | WO 01/03592 | 1/2001 |
| WO | WO 01/67974 | 9/2001 |

OTHER PUBLICATIONS

Office Action Received for Japanese Application No. 2007-500849, Dated Jun. 23, 2010, With An English Language Translation Attached.

Supplementary European Search Report for European Application No. EP 05 71 2901 performed on Nov. 17, 2008.

* cited by examiner

POLYAXIAL LOCKING SCREW PLATE ASSEMBLY

CROSS-REFERENCE TO RELATED APPLICATION

This application is a divisional application of U.S. patent application Ser. No. 10/788,098 which was filed on Feb. 26, 2004 now U.S. Pat. No. 7,311,712, the contents of which are incorporated by reference herein.

BACKGROUND OF THE INVENTION

This invention relates generally to a spinal implant assembly for holding adjacent vertebral bones fixed. More particularly, the present invention pertains to a spinal plate assembly which includes a mechanism for fixedly attaching and locking bone fixation screws to the plate at desired angles and for preventing back out of the screws from the plate.

SUMMARY OF THE INVENTION

The bone fixation assembly of the present invention includes a threaded screw shank and a screw head having upper and lower ends. The screw head lower end is secured to a proximal end of said screw shank. The screw head has substantially frustospherical shaped side surfaces and is split into segments at one of the ends. The head is radially expandable at the one end. An expansion screw is centrally received in the screw head. An interface between the expansion screw and the screw head forms a cam mechanism for expanding the screw head upon axial rotation of the expansion screw.

Further, the present invention provides a bone fixation screw comprising a threaded screw shank and a screw head secured to a proximal end of the screw shank. The screw head is split into segments at the screw head upper end. An expansion screw is centrally received in the upper end of the screw head. An interface between said expansion screw and said screw head forms a cam mechanism for expanding the screw head upon axial rotation of the expansion screw.

Also, the present invention provides a bone fixation screw comprising a screw shank and a screw head extending from a proximal end of the screw shank. The screw head comprises a generally frusto-spherically shaped body having a plurality of annularly spaced slots extending therearound and an axial bore extending therethrough. The axial bore has bore threads extending therethrough. An expansion screw is threadingly inserted into the axial bore. The expansion screw has a tapered length adapted to engage the bore threads of the axial bore and expand the screw head upon advancement of the expansion screw into the axial bore.

BRIEF DESCRIPTION OF THE DRAWINGS

The accompanying drawings show, for the purpose of exemplification, without limiting the scope of the invention or appended claims, certain practical embodiments of the present invention wherein:

DETAILED DESCRIPTION OF THE INVENTION

Although the invention is illustrated and described herein with reference to specific embodiments, the invention is not intended to be limited to the details shown. Rather, various modifications may be made in the details within the scope and range of equivalents of the claims and without departing from the invention.

Figure 3:
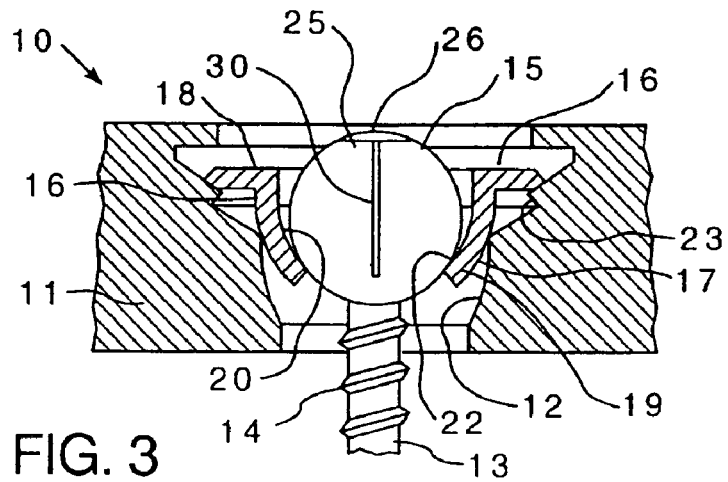
FIGS. 3, 4 and 5 are schematic sequence drawings illustrating the application of the bone fixation assembly of the present invention.
Figure 4:
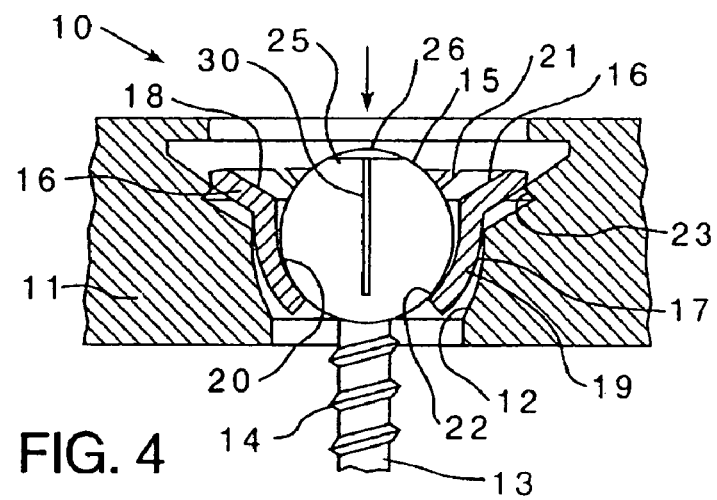
Figure 5:
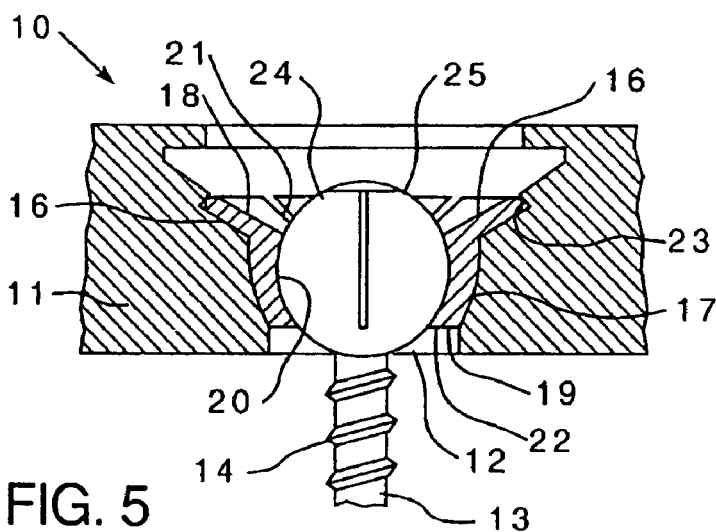

Referring first to sequence application FIGS. 3, 4 and 5, the bone fixation assembly 10 is illustrated. The bone fixation assembly 10 includes a fixation device 11, here illustrated as a bone fixation plate, having a through passage 12 and a fastening screw 13 having a threaded shaft 14 for insertion through the through passage 12 and threadable insertion into underlying bone (not shown). Screw 13 is further provided with head 15 having substantially frustospherical shaped side surfaces.

Figure 1:
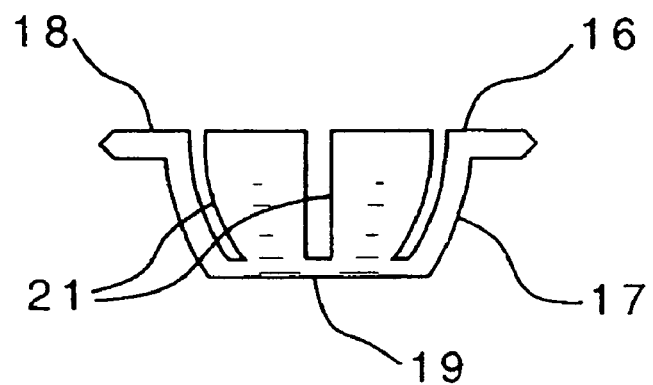
FIG. 1 is a view in front elevation of the bushing utilized in the bone fixation assembly of the present invention.
Figure 2:
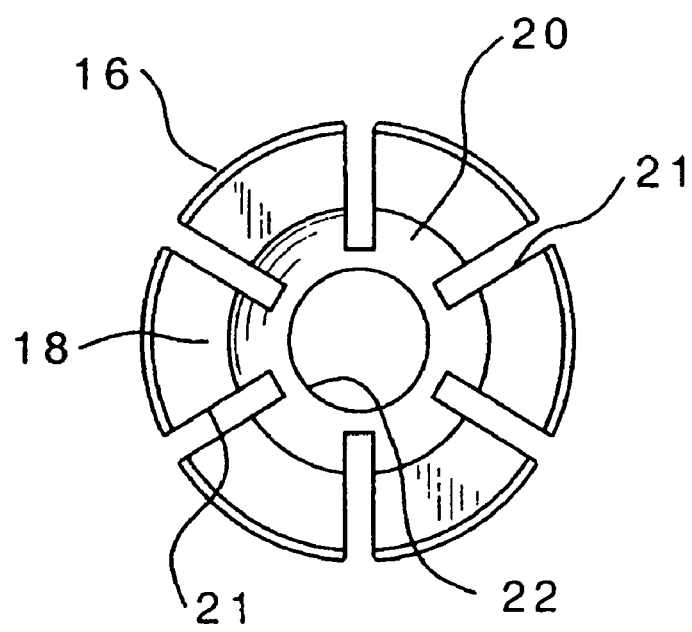
FIG. 2 is a top or plan view of the bushing shown in FIG. 1.

A bushing 16, which is also shown in detail in FIGS. 1 and 2, is provided and has an annular shaped side wall 17 having upper and lower ends 18 and 19 respectively. The side wall 17 defines an upwardly open interior bowl 20 for receiving screw head 15 therein. Annularly spaced slots 21 are provided in side wall 17 and depend downwardly from the upper end 18 for allowing inward compression of side wall 17 at upper end 18. A centrally located screw shank passage 22 is provided in the lower end 19 of bushing 16 for passage of screw shank 13 but not screw head 15.

Bowl 20 is configured and dimensioned for polyaxial rotation of screw head 15 therein and for preventing back out of the screw head when the side wall 17 is compressed inwardly about screw head 15 as is illustrated in FIG. 5. As is illustrated in FIGS. 3, 4 and 5, the through passage 12 is configured and dimensioned to downwardly receive the bushing therein as progressively illustrated in the three figures and represented by the downward arrow in FIG. 4 for thereby inwardly compressing bushing 16 about screw head 15 as is illustrated in the final representation of FIG. 5. An annular recess 23 is provided in through passage 12 and is configured and dimensioned to annularly receive the upper end 18 of bushing 16 under compression with a snap fit as is illustrated in FIG. 5 whereby the screw head 15 is retained in bowl 20 and is thereby prevented from backing out.

Figure 6:
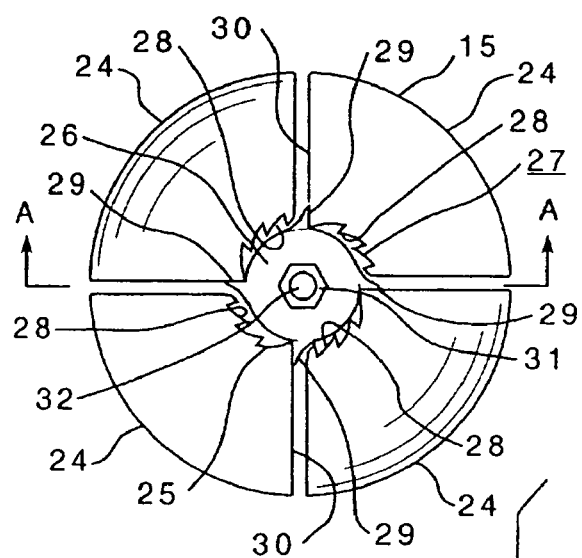
FIG. 6 is an enlarged top view of the bone fixation screw shown in FIGS. 3, 4 and 5.
Figure 7:
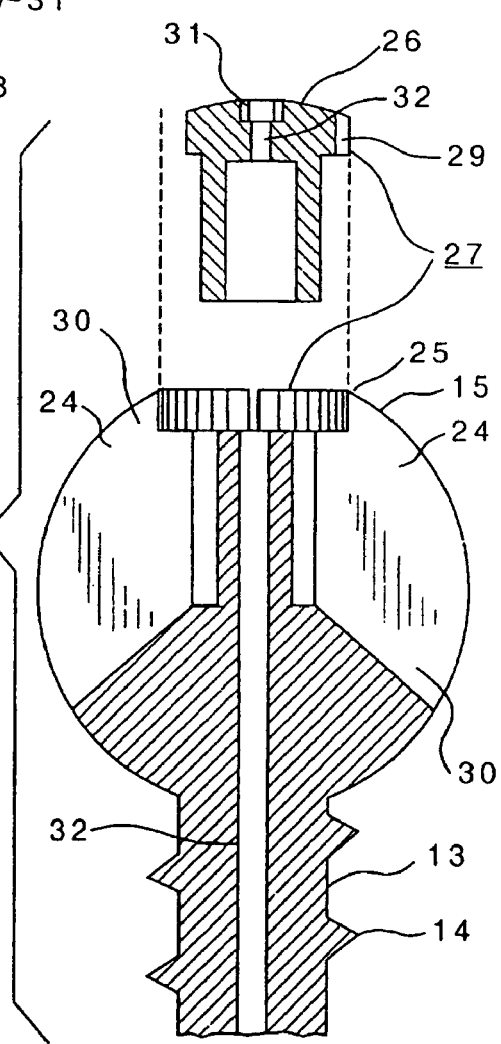
FIG. 7 is an exploded view in side elevation of the bone fixation screw shown in FIG. 6 as seen along section line A-A.

The detail of bone screw 13 is illustrated in FIGS. 6 and 7. As previously indicated, screw head 15 has substantially frustospherical shaped side surfaces and is split into four segments 24 at the upper end of screw head 15 by slots 30 whereby screw head 15 is radially expandable at its upper end 25. More or fewer segments are also permissible. An expansion pawl 26 is centrally and slidably received in the upper end 25 of screw head 15 for rotation, and a cam mechanism 27 is disposed between expansion pawl 26 and segmented screw head 15 for expanding screw head 15 upon axial rotation of expansion pawl 26.

As may be best seen in FIG. 6, the upper end 25 of screw head 15 is provided with multiple radially extending cam steps 28 for each of the head segments 24 and these cam steps 28 are provided in the form of teeth with intervening ramps that progressively converge inwardly toward expansion pawl 26 as one progresses in the counterclockwise direction. This cam mechanism 27 further includes four cam followers 29 radially protruding outwardly from the upper end of expansion pawl 26. These followers 29 are engaged against the respective segments 24 of screw head 15 and they are so prepositioned in the slots 30 providing segments 24 whereby when expansion pawl 26 is rotated clockwise by a screwdriver engaging the hex drive cavity 31 of the upper end of expansion pawl 26, the entire screw head 15 together with its threaded shaft 13 is rotated clockwise for driving the screw shank 14 downwardly into underlying bone.

Once the bone fixation screw 13 is fully secured as illustrated in FIG. 5, the outer expandable portion of the screw head 15 is stabilized with the outer Phillips-drive sleeve of a screwdriver (not shown), rotation of the expansion pawl 26 is advanced in a counterclockwise direction by an inner drive of the screwdriver whereby the cam followers 29 will progressively engage the cam steps 28 of each corresponding head segment 24. As these followers 29 progressively engage the cam steps 28, the upper end of head 15 is annularly expanded to thereby lock the screw 13 from further polyaxial rotation within the bowl 20 of bushing 16. The cam followers 29 and the cam steps 28 are configured and dimensioned whereby full expansion and locking of the screw head within the assembly 10 is accomplished with less than a quarter counterclockwise turn of the expansion pawl 26.

The bone fixation screw 13 is fully cannulated as illustrated by the central cannulation passage 32 to permit the use of guide wires during the surgical procedure.

Figure 8:
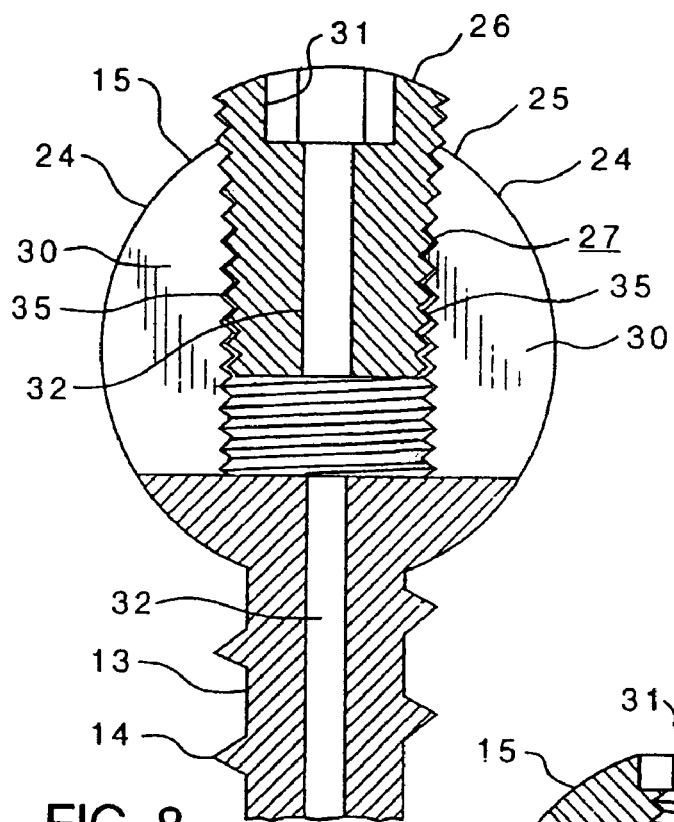
FIG. 8 is an enlarged view shown in vertical mid cross section illustrating another embodiment of the bone fixation screw shown in the previous figures.

Turning next to FIG. 8, another embodiment of the screw 13 is illustrated wherein the expandable head 15 is here expanded by the cam mechanism 27 which includes axially extending cam ramps 35, as opposed to radially extending cam ramps shown in the illustration of FIGS. 6 and 7. Here the axially extending cam ramps are in the form of tapered sides on expansion screw 26.

Figure 9:
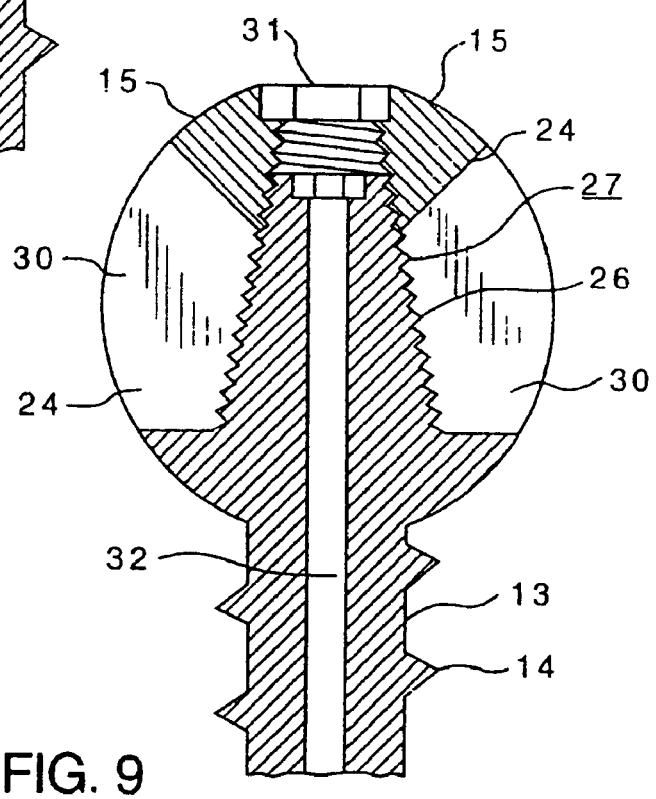
FIG. 9 is an enlarged view in vertical mid cross section illustrating yet another embodiment of the bone fixation screw of the present invention.

Yet another embodiment is illustrated in FIG. 9 in which head 15 is segmented at the bottom end thereof instead of at the top, and the cam mechanism 27 includes an expansion screw 26 which in this instance is secured to the upper end of screw shank 13 and is also provided with tapered sides to thereby expand the four segments 24 of screw head 15 at the bottom end thereof to lock the screw head 15 from further polyaxial rotation.

What is claimed:

1. A bone fixation screw comprising:
   a threaded screw shank and a screw head having upper and lower ends with said screw head lower end secured to a proximal end of said screw shank, said screw head having substantially frustospherical shaped side surfaces and split into segments at the upper end, each segment having an end, the screw head having an axial bore extending therethrough, whereby said head is radially expandable at said upper end; and
   an expansion pawl centrally received in said screw head, the screw head comprising a plurality of teeth positioned along the ends of the segments of the screw head, the ends of the segments facing the axial bore, the teeth extending into the axial bore radially inwardly with respect to a circle defined by the ends of the segments, each of the teeth extending in a direction toward the expansion pawl, each of the teeth forming a cam mechanism for expanding said screw head upon axial rotation of said expansion pawl.

2. The bone fixation screw of claim 1, wherein said screw head comprises four segments.

3. A bone fixation screw comprising:
   a threaded screw shank and a screw head secured to a proximal end of said screw shank, said screw head having an upper end and being split into segments at said screw head upper end, each segment having an end, the screw head having an axial bore extending therethrough; and
   an expansion pawl centrally received in the upper end of said screw head, the screw head comprising a plurality of teeth positioned along the ends of the segments of the screw head, the ends of the segments facing the axial bore, the teeth extending into the axial bore radially inwardly with respect to a circle defined by the ends of the segments, each of the teeth extending in a direction toward the expansion pawl, each of the teeth forming a cam mechanism for expanding said screw head upon axial rotation of said expansion pawl.

4. The bone fixation screw of claim 3, wherein said screw head has substantially frustospherical side surfaces.

5. The bone fixation screw according to claim 3, wherein said screw shank comprises a screw shank cannulation passage extending axially therethrough.

6. The bone fixation screw according to claim 5, wherein said expansion pawl comprises an expansion pawl cannulation passage extending axially therethrough, said expansion pawl cannulation passage being in communication with said screw shank cannulation passage.

7. A bone fixation screw comprising:
   a screw shank;
   a screw head extending from a proximal end of said screw shank, said screw head comprising a plurality of annularly spaced slots extending therearound and an axial bore extending therethrough, said screw head split into segments, each segment having an end, said segments comprising a plurality of teeth positioned along the ends of the segments of the screw head, the ends facing the axial bore, the teeth extending into the axial bore radially inwardly with respect to a circle defined by the ends of the segments; and
   an expansion pawl inserted into said axial bore, said expansion pawl having a plurality of followers adapted to engage the radially extending teeth of said axial bore and expand said screw head upon rotation of the expansion pawl in said axial bore.

8. The bone fixation screw according to claim 7, wherein said screw shank comprises a screw shank cannulation passage extending axially therethrough in communication with the axial bore of said screw head.

9. The bone fixation screw according to claim 7, wherein said expansion pawl comprises an expansion pawl cannulation passage extending axially therethrough.

10. The bone fixation screw according to claim 7, wherein the expansion pawl is axially rotatable in the bore in a first direction to rotate the screw head and screw shank and drive the bone fixation screw into bone, the expansion pawl axially rotatable in the bore in a second direction opposite the first direction to progressively engage the followers with the radially extending teeth and expand the screw head to lock the screw head within an assembly.

11. The bone fixation screw according to claim 7, wherein the plurality of followers are each positionable within one of the annularly spaced slots for rotating the screw head and screw shank when the expansion pawl is rotated.

12. The bone fixation screw according to claim 7, wherein the plurality of followers comprise four followers radially protruding outwardly from the expansion pawl.

13. The bone fixation screw according to claim 7, wherein the annularly spaced slots split the screw head into four segments.

14. The bone fixation screw according to claim 13, wherein the plurality of followers comprise four followers, each follower engaged with one of the four segments, and each segment engaged with one of the four followers.

15. The bone fixation screw according to claim 7, wherein the expansion pawl comprises a cavity for receiving a driving instrument.

16. A bone fixation screw comprising:
   a threaded screw shank and a screw head having upper and lower ends with said screw head lower end secured to a proximal end of said screw shank, said screw head having substantially frustospherical shaped side surfaces and split into segments, each segment having an end, the screw head having an axial bore extending therethrough, whereby said head is radially expandable; and
   an expansion pawl centrally received in said screw head, the screw head comprising a plurality of ratchet teeth positioned along the ends of the segments of the screw head, the ends of the segments facing the axial bore, the ratchet teeth extending into the axial bore radially inwardly with respect to a circle defined by the ends of the segments, each of the teeth extending in a direction toward the expansion pawl, each of the teeth forming a cam mechanism for expanding said screw head upon axial rotation of said expansion pawl.

\* \* \* \* \*